(12) United States Patent
Sullivan

(10) Patent No.: US 7,421,789 B1
(45) Date of Patent: Sep. 9, 2008

(54) SYSTEMS AND METHODS FOR FOOTWEAR RELATED MEASUREMENT AND ADJUSTMENT

(75) Inventor: Sean Sullivan, La Selva Bch, CA (US)

(73) Assignee: Somnio, Inc., Aptos, CA (US)

( * ) Notice: Subject to any disclaimer, the term of this patent is extended or adjusted under 35 U.S.C. 154(b) by 0 days.

(21) Appl. No.: 11/779,943

(22) Filed: Jul. 19, 2007

(51) Int. Cl.
*A43D 1/02* (2006.01)
*A61B 5/107* (2006.01)

(52) U.S. Cl. .............................. 33/3 R; 33/511; 33/515; 33/3 B; 33/3 C

(58) Field of Classification Search ............... 33/3 R, 33/3 A, 3 B, 3 C, 511, 512, 515, 4, 5, 6, 806, 33/832, 300
See application file for complete search history.

(56) References Cited

U.S. PATENT DOCUMENTS

| | | | |
|---|---|---|---|
| 2,535,787 A | 12/1950 | Darby | |
| 4,227,311 A * | 10/1980 | Behney | ........................ 33/3 C |
| 4,662,079 A | 5/1987 | Graf et al. | |
| 4,669,142 A | 6/1987 | Meyer | |
| 4,756,096 A | 7/1988 | Meyer | |
| 4,807,368 A * | 2/1989 | Beyl | ........................ 33/3 B |
| 4,821,420 A * | 4/1989 | Maykel | ........................ 33/512 |
| 5,689,446 A * | 11/1997 | Sundman et al. | ........................ 33/3 R |
| 7,069,665 B1 | 7/2006 | Adriano | |
| 7,082,697 B2 | 8/2006 | Ellis, III | |
| 7,125,509 B1 * | 10/2006 | Smith | ........................ 33/515 |
| 7,281,333 B2 * | 10/2007 | Caulliez et al. | ........................ 33/3 A |
| 2003/0014881 A1 | 1/2003 | Hay | |
| 2004/0193075 A1 | 9/2004 | Martindale | |
| 2006/0080862 A1 | 4/2006 | Hay et al. | |
| 2006/0227337 A1 * | 10/2006 | Sundman et al. | ............ 356/601 |
| 2006/0277772 A1 * | 12/2006 | Pupko | ........................ 33/3 R |
| 2006/0283243 A1 | 12/2006 | Peterson | |
| 2007/0253004 A1 * | 11/2007 | Danenberg et al. | .......... 356/635 |

OTHER PUBLICATIONS

ALINE foot measuring device (attached).
Brannock foot measuring device (attached).

* cited by examiner

*Primary Examiner*—Yaritza Guadalupe-McCall
(74) *Attorney, Agent, or Firm*—Trent H. Baker; Baker & Associates PLLC

(57) ABSTRACT

One embodiment of the present invention relates to a footwear characteristic measuring system designed to determine measurements of a particular footwear wedge insert which may be used to encourage correct knee alignment in an article of footwear. The system includes a base, a recess, a set of angled members, and an illumination device. The recess is disposed within the base and is sized such that a user's foot may be disposed within the recess. The illumination device is disposed on the base and is medially aligned with the recess. The illumination device is oriented so as to transmit an illumination output upward or perpendicular to the top surface of the base. The angled members include an angled top surface and are configured to reliably couple within the recess of the base. A second embodiment of the present invention relates to a method of encouraging correct knee and ankle alignment in an article of footwear.

20 Claims, 4 Drawing Sheets

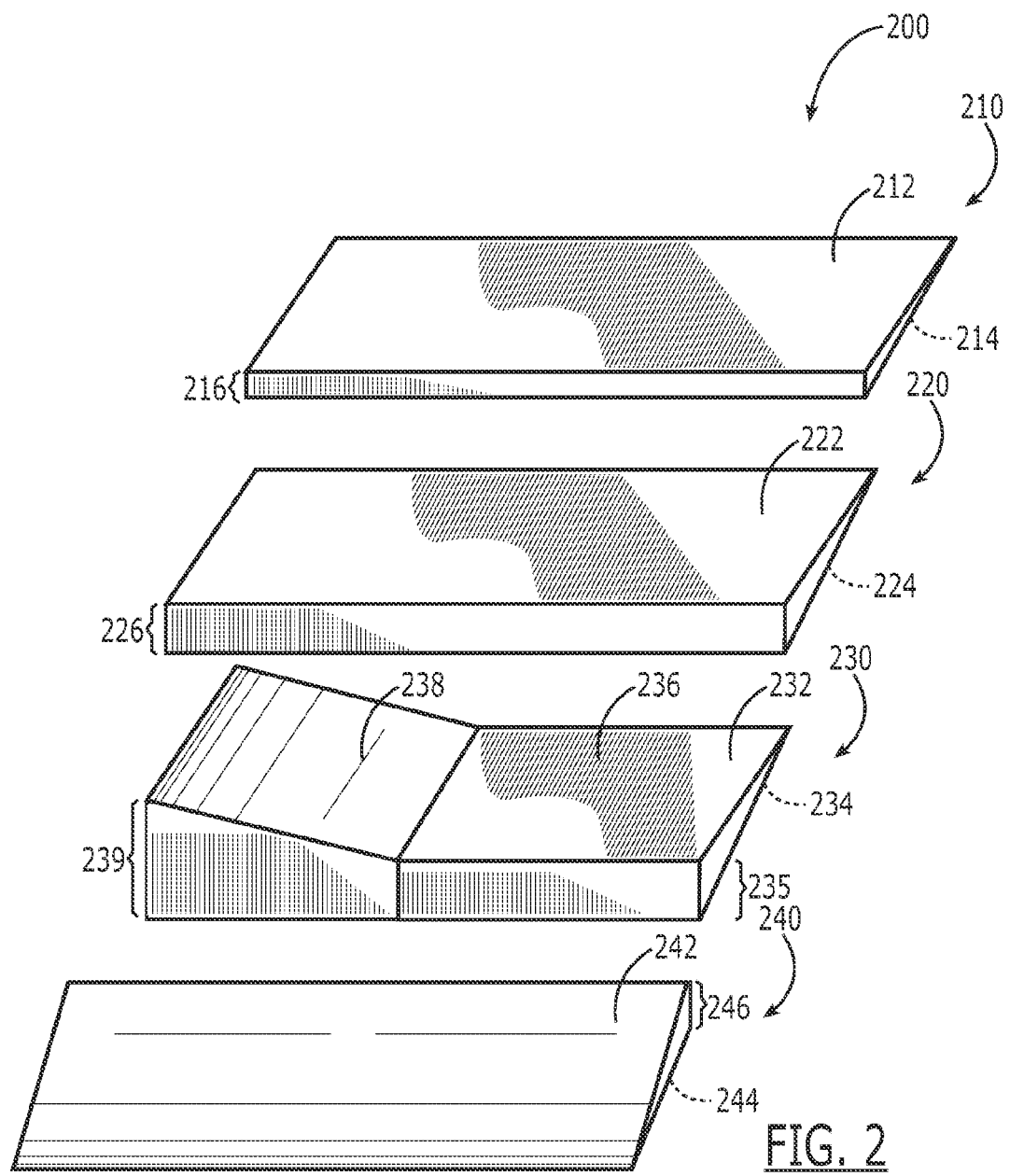

SYSTEMS AND METHODS FOR FOOTWEAR RELATED MEASUREMENT AND ADJUSTMENT

FIELD OF THE INVENTION

The invention generally relates to footwear including shoes, boots, sandals, etc. In particular, the present invention relates to systems and methods for properly measuring, aligning, fitting, and adjusting feet and footwear.

BACKGROUND OF THE INVENTION

Footwear refers to articles worn on the foot of a user, including shoes, boots, sandals, etc. Footwear provides a supportive platform between the sole of user's foot and the ground to facilitate protection and alignment. For example, a pair of sandals protects a user's foot from abrasion and damage caused by debris or bacteria on the ground. In addition, a boot or shoe may support/align a user's foot and lower leg according to specific parameters. Footwear is generally designed to provide protection and support corresponding to a set of intended uses. For example, a trail running shoe is often designed to both protect and support a user's foot from conditions encountered while engaged in the activity of trail running. Protection refers to protecting both the skin and internal muscles of the foot. Alignment refers to maintaining or encouraging a user toward proper foot and body alignment.

One of the challenges of footwear design is the need to accommodate a wide variety of foot shapes and dimensions while providing a product that is economical. A second major challenge is the proper selection of an appropriate set of available footwear for a particular individual and activity. Human feet tend to encompass a wide variety of characteristics including volume, length, arch height, toe dimensions, and various protrusions. The variance in these characteristics causes people's feet to differ significantly from one another and sometimes from foot to foot. To properly provide optimal support characteristics, it is necessary for the article of footwear to correspond as closely as possible to the unique dimensions of a user's foot. An improperly-fitting article of footwear will likely cause pain, injury and damage to a user's foot, leg(s), back, and neck. Therefore, various systems and methods are used to facilitate selecting and/or adjusting existing footwear for a user.

Unfortunately, conventional measuring systems and methods fail to measure all of the variables necessary to select and/or adjust an article of footwear for optimal fit. One of the most common measuring devices measures only three foot characteristics including heel to toe, arch location, and width. These characteristics are then used to select an existing article of footwear. Other adjustments are often handled through a manual trial and error system in which a user tries on a pair of shoes and problems are resolved through making various adjustments. Unfortunately, this process is not reliable for addressing the needs of a user in adjusting or selecting appropriate footwear.

Therefore, there is a need in the industry for systems and methods of measuring and adjusting footwear to accommodate the unique podiatric needs of a user.

SUMMARY OF THE INVENTION

The present invention relates to footwear including shoes, boots, sandals, etc. In particular, the present invention relates to systems and methods for properly measuring, aligning, fitting, and adjusting feet and footwear. One embodiment of the present invention relates to a footwear characteristic measuring system designed to determine measurements of a particular footwear wedge insert which may be used to encourage correct knee alignment in an article of footwear. The system includes a base, a recess, a set of angled members, and an illumination device. The recess is disposed within the base and is sized such that a user's foot may be disposed within the recess. The illumination device is disposed on the base and is medially aligned with the recess. The illumination device is oriented so as to transmit an illumination output upward or perpendicular to the top surface of the base. The angled members include an angled top surface and are configured to reliably couple within the recess of the base. A second embodiment of the present invention relates to a method of encouraging correct knee and ankle alignment in an article of footwear. The method includes transmitting an illumination device upward and articulating a user's knee and ankle until the user's knee is medially illuminated. If it is necessary to laterally articulate the user's ankle (varus or valgus), the method further includes interchangeably positioning angled members below the user's foot until the user's knee is illuminated without lateral ankle articulation, and positioning a corresponding angled member within an article of footwear so as to encourage proper knee alignment.

Embodiments of the present invention represent a significant advance in footwear measuring and fitting technology. Conventional systems and methods fail to accurately and reliably measure feet in relation to knee positioning for adjusting varus and valgus ankle articulation. Likewise, conventional footwear does not accommodate the unique varus and valgus slopes necessary to encourage proper alignment for numerous users.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE DRAWINGS

The following description of the invention can be understood in light of the Figures, which illustrate specific aspects of the invention and are a part of the specification. Together with the following description, the Figures demonstrate and explain the principles of the invention. In the Figures, the physical dimensions may be exaggerated for clarity. The same reference numerals in different drawings represent the same element, and thus their descriptions will be omitted.

FIG. 2 illustrates a plurality of angled members for use in conjunction with the footwear measuring system illustrated in FIG. 1.

DETAILED DESCRIPTION OF THE INVENTION

Figure 1:
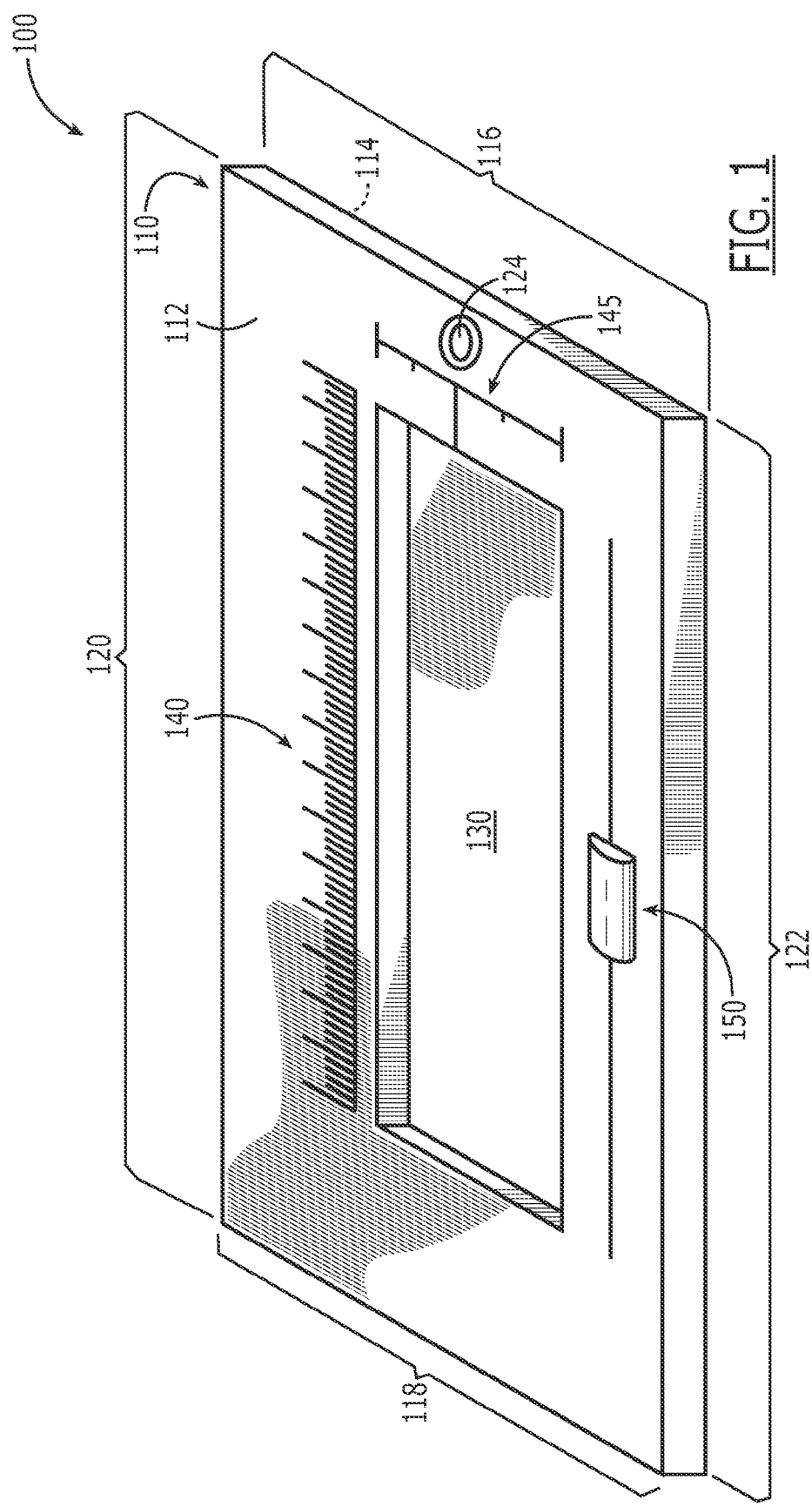
FIG. 1 illustrates a perspective view of a footwear characteristic measuring system in accordance with one embodiment of the present invention.

The present invention relates to footwear including shoes, boots, sandals, etc. In particular, the present invention relates to systems and methods for properly measuring, aligning, fitting, and adjusting feet and footwear. One embodiment of the present invention relates to a footwear characteristic measuring system designed to determine measurements of a particular footwear wedge insert which may be used to encourage correct knee alignment in an article of footwear. The system includes a base, a recess, a set of angled members, and an illumination device. The recess is disposed within the base and is sized such that a user's foot may be disposed within the recess. The illumination device is disposed on the base and is medially aligned with the recess. The illumination device is oriented so as to transmit an illumination output upward or perpendicular to the top surface of the base. The angled members include an angled top surface and are configured to reliably couple within the recess of the base. A second embodiment of the present invention relates to a method of encouraging correct knee and ankle alignment in an article of footwear. The method includes transmitting an illumination device upward and articulating a user's knee and ankle until the user's knee is medially illuminated. If it is necessary to laterally articulate the user's ankle (varus or valgus), the method further includes interchangeably positioning angled members below the user's foot until the user's knee is illuminated without lateral ankle articulation, and positioning a corresponding angled member within an article of footwear so as to encourage proper knee alignment. Also, while embodiments are described in reference to footwear, it will be appreciated that the teachings of the present invention are application to other areas.

The following terms are defined as follows:

Footwear—Any type of covering, protecting, and/or supporting structure designed to at least partially cover the foot of a user including but not limited to shoes, sandals, boots, clogs, slippers, etc.

Correlated illumination device—An illumination device that produces a substantially correlated illumination output including but not limited to a laser and a bulb with a set of correlating optics.

Knee articulation—For purposes of this application the term "knee articulation" refers simple to bending of the knee in the medial plane. Any lateral knee articulation is discussed with reference to any associated lateral ankle articulation, as described below.

Ankle articulation—the human ankle is able to articulate in a plurality of directions and orientations. For purposes of this application, the term "lateral articulation" refers to varus and valgus articulation, also commonly associated with the terms supination and pronation. Non-lateral ankle articulation or otherwise non-designated ankle articulation refers to plantar flexion and dorsiflexion in the medial plane, also commonly associated with forward and rearward articulation.

Reference is initially made to FIG. 1, which illustrates a perspective view of a footwear characteristic measuring system, designated generally at 100. The system 100 includes a base 110, a recess 130, a correlated illumination device 124, a plurality of angled members (illustrated and described with reference to FIG. 2), a length measurement system 140, a medial alignment system 145, and an arch height measurement system 150. The base 110 includes a top surface 112, a bottom surface 114, a front end 116, a rear end 118, a left medial side 120, and a right medial side. The base 110 may be composed of materials including metal and plastic. The recess 130 is disposed on the top surface 112 of the base 110 between the front and rear ends 116, 118 and may optionally extend through or up to the bottom surface 114. The correlated illumination device 124 is also disposed on the top surface 112 of the base 110 between the front and rear ends 116, 118. The recess 130 and the correlated illumination device 124 are medially aligned on the top surface 112 of the base 110 between the left and right medial sides 120, 122. The illustrated correlated illumination device 124 is a laser oriented upward and substantially perpendicular to the top surface 112 of the base 110. Although not illustrated, the correlated illumination device may include a power supply and electrical switching mechanism housed within the base 110. Various technologies and/or techniques may be utilized to produce a completely visible light beam including dust dispersement and/or low ambient lighting. Likewise, the bottom of the recess 130 may include a touch sensitive switching mechanism configured to automatically illuminate the correlated illumination device 124 in response to the weighting of the recess associated with a user positioning their foot within the recess 130 or on top of an angled member (See FIG. 2) disposed within the recess 130.

The optional length measurement system 140, medial alignment system 145, and arch height measurement system 150 are also disposed on the top surface 112 of the base 110 as illustrated. The length measurement system 140 includes a set of incremental length measurement marks along the corresponding left medial 120 side of the recess 130 incrementally ascending from the corresponding front side 116 of the recess 130. The function of the length measurement system 140 is to both measure the length of a user's foot disposed within the recess and encourage a repeatable placement/orientation of the user's foot in the recess. Likewise, the medial alignment system 145 is disposed on the corresponding front side 116 of the recess 130. The medial alignment system 145 includes a set of designation marks. The medial alignment system 145 functions as a medial or width measurement system of the user's foot in addition to encouraging proper medial alignment of the user's foot within the recess with respect to the left and right medial sides 120, 122. The arch height measurement system 150 is also disposed on the top surface 112 of the base 110 corresponding to the right medial side 122 of the recess 130. The arch height measurement system includes a slidably adjustable member that assists in reliably and accurately measuring the location of a foot's arch. The location of the slidable adjustable member may be correlated with the length measurement system's marks to identify the location of the arch with respect to the front of the foot.

Reference is next made to FIG. 2, which illustrates a plurality of angled members for use in conjunction with the footwear measuring system illustrated in FIG. 1, designated generally at 200. The angled members 200 are configured to be releasably coupled within the recess 130 of the system 100. The angled members 200 are shaped so as to create a keyed releasable coupling with the recess for purposes of reliable and repeatable positioning and engagement. The angled members 200 are configured to support the weight of a user without significant deformation. The first angled member 210 includes a top surface 212, a bottom surface 214, and a wedge height 216. The wedge height 216 corresponds to the medial angle, creating a sloped top surface 212. The second angled member 220 also includes a top surface 222, a bottom surface 224, and a wedge height 226. It will be appreciated that the second angled member 220 has a larger wedge height 226 than the first angled member's 210 wedge height 216. The third angled member 230 includes a front component member 236 and a rear component member 238, a top surface 232, a bottom surface 234, a rear wedge height 239, and a front wedge height 235. The front and rear component members 236, 238 are shaped to facilitate the releasable keyed coupling with the recess 130 and one another. The rear component member 238 includes a lengthwise slope while the front component member 236 includes a lateral slope. Various wedge slope component members may be utilized in accordance with the teachings of the present invention. The fourth angled member 240 also includes a top surface 242, a bottom surface 244, and a wedge height 246. The fourth angled member 240 includes an oppositely oriented sloped top surface 242. Various alternative systems may be utilized so that individual angled members and components members may be rotated with respect to the recess so as to create a wide variety of sloped top surfaces.

Figure 3A:
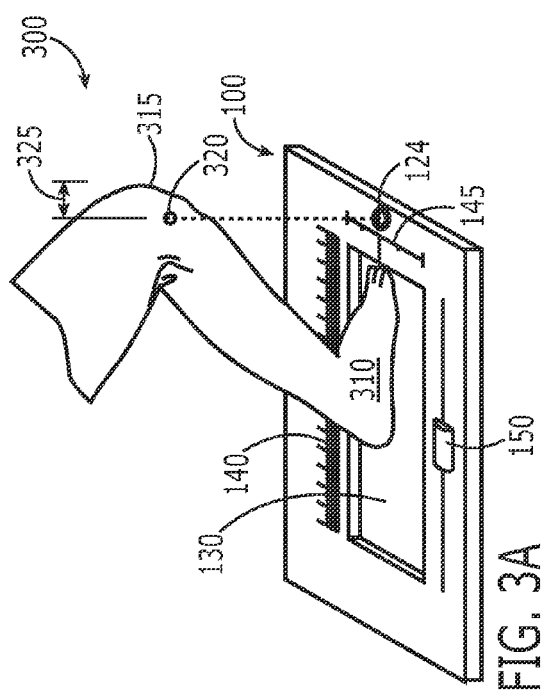
FIGS. 3A-3D illustrate a series of perspective views detailing a method of encouraging correct alignment in an article of footwear in accordance with a second embodiment of the present invention.
Figure 3B:
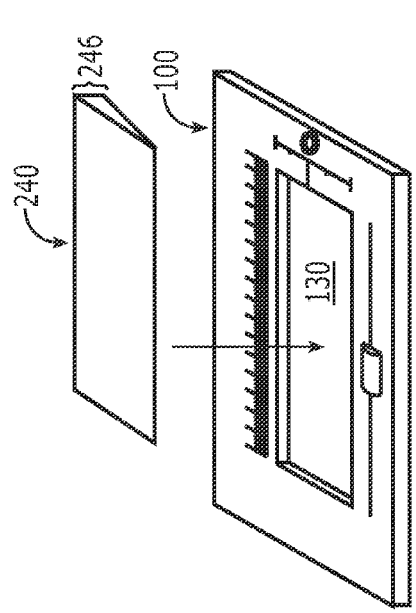
Figure 3C:
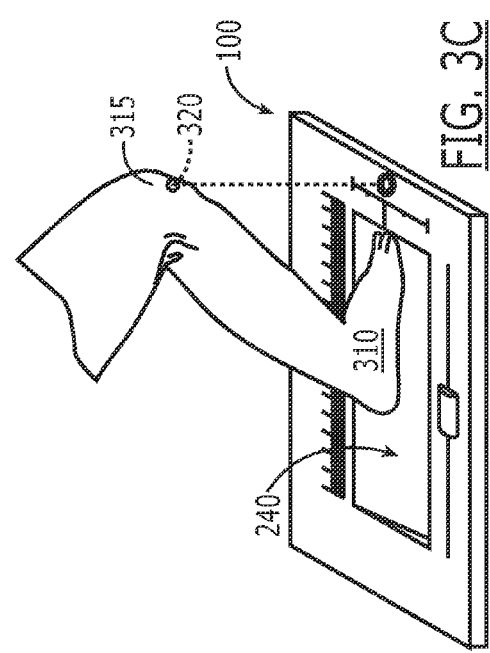
Figure 3D:
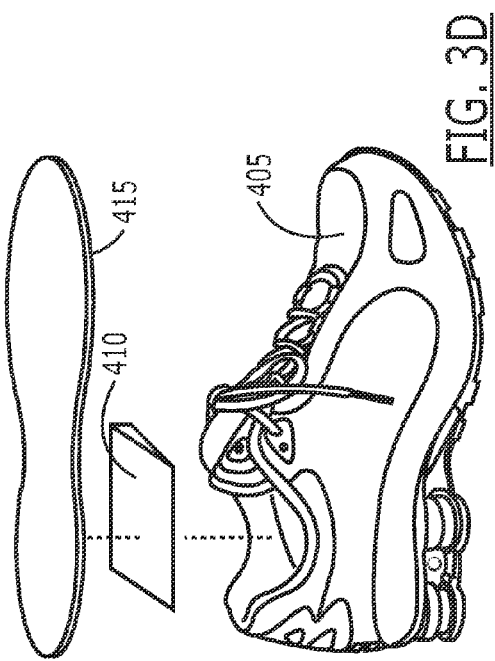

Reference is next made to FIGS. 3A-3D, which illustrate a series of perspective views detailing a method of encouraging correct alignment in an article of footwear. FIG. 3A illustrates a user's foot 310 positioned within the recess 130 of the system 100. The foot 310 is medially and frontward oriented with respect to the recess 130. The user's knee 315 is articulated to position the knee 315 in lengthwise orientation corresponding to the correlated illumination device 124. The correlated illumination device 124 created an illumination output 320 on the user's knee 315. In FIG. 3A the correlated illumination output 320 is medially offset from the center of the user's knee 315 a distance 325 and therefore would require a lateral ankle articulation to center the correlated illumination output 320 with respect to the user's knee. This indicates the need for some form of lateral ankle adjustment in the user's footwear to encourage proper alignment of the knee 315. FIG. 3B illustrates positioning an angled member 240 with a wedge height 246 within the recess 130 of the system 100. FIG. 3C then illustrates again positioning the user's foot 310 within the recess 130 on top of the angled member 240 and articulating the knee 315 and ankle forward to be illuminated by the correlated illumination output 320. As illustrated, the angled member 240 corrected the offset distance by medially aligning the correlated illumination output 320 with respect to the lateral location of the knee 315. Various iterations may be performed to select the proper angled member that best corrects the offset distance 325. FIG. 3D illustrates the positioning of a corresponding insert 410 within an article of footwear 405. The corresponding insert includes a wedge height corresponding to the wedge height 246 of the successfully angled member 240 that corrected the offset distance 325. The corresponding insert 410 is positioned between the internal removable sole 415 and the internal lower surface of the article of footwear 405. A subsequent process may be performed for the opposite foot. The internal removable sole 415 may include a region configured to receive the corresponding insert 410 so as to prevent lateral movement. The region may create a sandwiched, keyed coupling between the corresponding internal removable sole 415, the corresponding insert 410, and the internal lower surface of the article of footwear 405.

Figure 4:
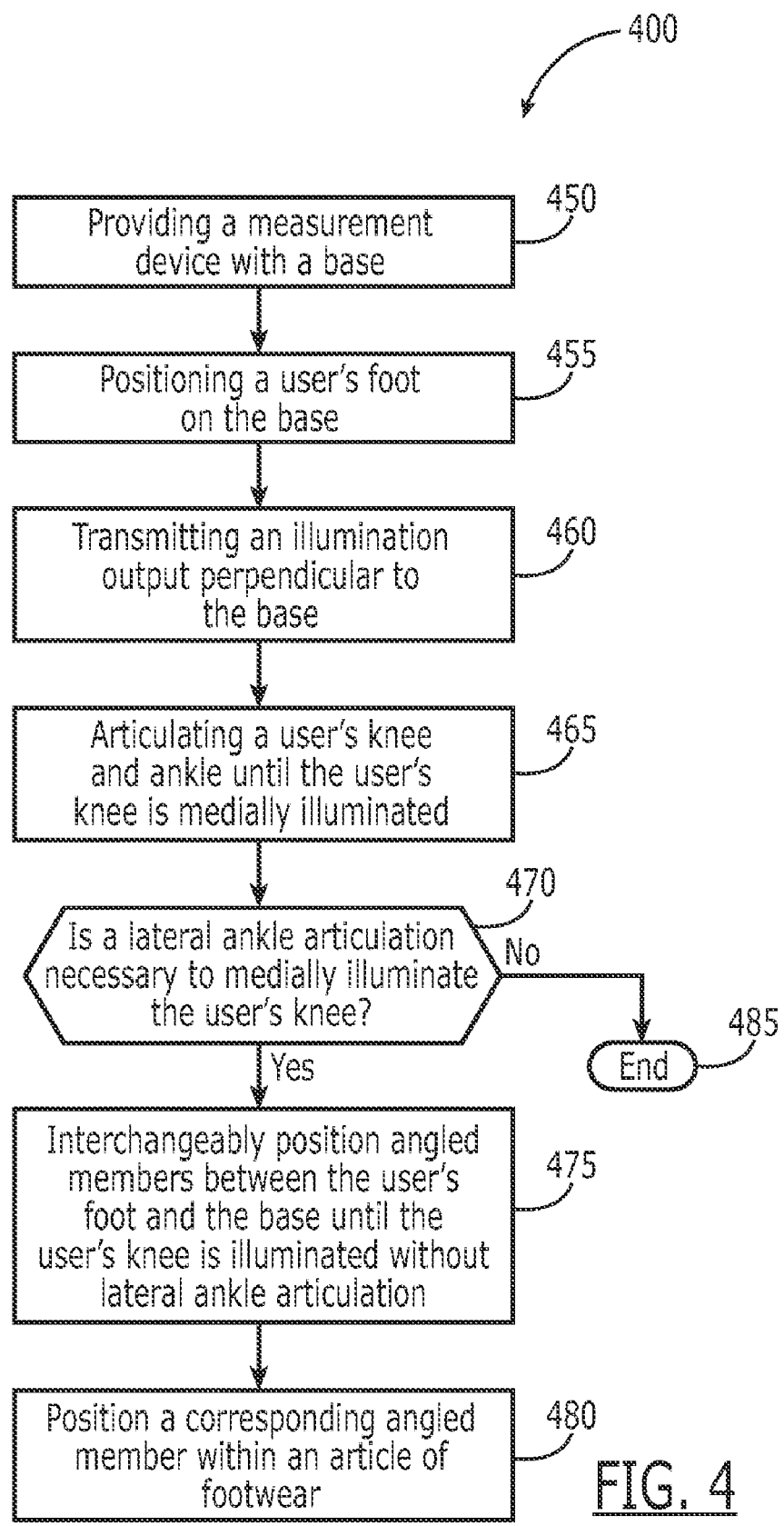
FIG. 4 illustrates a flow chart of a method of encouraging correct alignment in an article of footwear in accordance with a second embodiment of the present invention.

Reference is next made to FIG. 4, which illustrates a flow chart of a method of encouraging correct alignment in an article of footwear, designated generally at 400. First, providing a measurement device with a base, act 450. The measurement device may be the system illustrated in FIGS. 1-2. A user's foot is positioned on the base, act 455. An illumination output is transmitted perpendicular to the base, act 460. The user's knee and ankle are articulated to illuminate to the user's knee, act 465. A determination is made if it is necessary to laterally articulate the user's ankle to medially illuminate the user's knee, act 470. If the determination is affirmative, the method further includes interchangeably positioning angled members between the user's foot and the base until the user's knee is illuminated without lateral ankle articulation, act 475, and positioning a corresponding angled member within an article of footwear, act 480.

What is claimed is:
1. A footwear characteristic measuring system comprising:
a base having a top surface, a bottom surface, a front end, and a rear end;
a recess disposed on the top surface of the base between the front end and rear end;
a plurality of angled members configured to be interchangeably disposed within the recess with a releasable keyed coupling such that the positioning of the angled members is substantially repeatable with respect to the base; and
a correlated illumination device disposed on the top surface of the base in proximity to the front end, wherein the correlated illumination device is medially aligned with the recess with respect to the top surface, and wherein the correlated illumination device is configured to create an illumination output path substantially perpendicular to the top surface of the base.

2. The system of claim 1, wherein the base further includes an incremental length measurement system ascending from the front end of the base.

3. The system of claim 1, wherein base further includes an arch height measurement system.

4. The system of claim 1, wherein the base further includes a medial alignment system corresponding to the recess.

5. The system of claim 1, wherein the recess is two dimensionally larger than the bottom surface of a user's foot.

6. The system of claim 1, wherein the recess extends through both the top surface and bottom surface of the base.

7. The system of claim 1, wherein each angled member includes an angled top surface, a substantially flat bottom surface, a front end, and a rear end, and when releasably coupled to the base, the front end of the angled member is aligned with the front end of the base.

8. The system of claim 7, wherein the angled top surface includes a uniform medial angle between the front end and the rear end of the angled member such that the top surface slopes from a particular height on one medial side down toward the opposite medial side of the angled member.

9. The system of claim 7, wherein the angled member includes a plurality of component angled members configured to key together so as to form the releasable keyed coupling within the recess of the base, and wherein each of the component angled members includes a unique angled top surface characteristic.

10. The system of claim 7, wherein the two dimensional size and shape of the bottom surface of each angled member corresponds to the two dimensional size and shape of the recess so as to facilitate the releasable keyed coupling.

11. The system of claim 1, wherein the correlated illumination device is a laser.

12. The system of claim 1, wherein the correlated illumination device further includes:
an illumination component configured to electrically generate an illumination output;
an electrical switching mechanism to select between an on and off state; and
a power supply electrically coupled to the illumination component and the electrical switching mechanism.

13. A footwear characteristic measuring system comprising:

a base having a top surface, a bottom surface, a front end, and a rear end, wherein the base further includes an incremental length measurement system ascending from the front end of the base;

a recess disposed on the top surface of the base between the front end and rear end, wherein the recess is two dimensionally larger than the bottom surface of a user's foot;

a plurality of angled members configured to be interchangeably disposed within the recess with a releasable keyed coupling such that the positioning of the angled members is substantially repeatable with respect to the base, wherein each angled member includes an angled top surface, a substantially flat bottom surface, a front end, and a rear end, and when releasably coupled to the base, the front end of the angled member is aligned with the front end of the base, wherein the two dimensional size and shape of the bottom surface of each angled member corresponds to the two dimensional size and shape of the recess so as to facilitate the releasable keyed coupling; and a laser disposed on the top surface of the base in proximity to the front end, wherein the laser is medially aligned with the recess with respect to the top surface, and wherein the correlated illumination device is configured to create an illumination output path substantially perpendicular to the top surface of the base.

14. A method of encouraging correct alignment in an article of footwear including the acts of:

providing a measurement device including a base;

positioning a user's foot on a top surface of the base;

transmitting an illumination output perpendicular to the top surface of the base;

articulating the user's knee and ankle until the user's knee is medially illuminated;

if a lateral articulation of the user's ankle is necessary to medially illuminate the user's knee, performing the following acts:

interchangeably positioning at least one angled member within the recess of the base beneath the user's foot until the user's knee is medially illuminated without laterally articulating the user's ankle; and positioning a corresponding final angled member within an article of footwear, wherein the final angled member enabled medial illumination of the user's knee without lateral articulation of the user's ankle.

15. The method of claim 14, wherein the act of providing a measurement device further includes providing a footwear characteristic measuring system comprising:

a base having a top surface, a bottom surface, a front end, and a rear end;

a recess disposed on the top surface of the base between the front end and rear end;

a plurality of angled members configured to be interchangeably disposed within the recess with a releasable keyed coupling such that the positioning of the angled members is substantially repeatable with respect to the base;

a correlated illumination device disposed on the top surface of the base in proximity to the front end, wherein the correlated illumination device is medially aligned with the recess with respect to the top surface, and wherein the correlated illumination device is configured to create an illumination output path substantially perpendicular to the top surface of the base.

16. The method of claim 14, wherein the act of positioning a user's foot within the recess of the base includes positioning the user's foot such that a front most portion of the user's foot is substantially disposed at the front most portion of the recess.

17. The method of claim 14, wherein the act of positioning a user's foot within the recess of the base includes medially aligning the user's foot with respect to the recess and base.

18. The method of claim 14, wherein the act of interchangeably positioning at least one angled member within the recess of the base beneath the user's foot until the user's knee is medially illuminated without laterally articulating the user's ankle, further includes engaging a releasable keyed coupling between the at least one angled member and the recess of the base.

19. The method of claim 14, wherein the act of interchangeably positioning at least one angled member within the recess of the base beneath the user's foot until the user's knee is medially illuminated without laterally articulating the user's ankle, further includes selecting an angled member with a medial slope oppositely corresponding to the ankle articulation direction necessary for the user to medial align the illumination output so as to correct the offset the necessary ankle articulation.

20. The method of claim 14, wherein the act of positioning a corresponding final angled member within an article of footwear, wherein the final angled member enabled medial illumination of the user's knee without lateral articulation of the user's ankle, further includes positioning the final angled member between an internal removable sole and an internal base of an article of footwear.

* * * * *